US012106472B2

(12) United States Patent
Huang et al.

(10) Patent No.: US 12,106,472 B2
(45) Date of Patent: Oct. 1, 2024

(54) EYE STATE ASSESSMENT METHOD AND ELECTRONIC DEVICE

(71) Applicants: Acer Incorporated, New Taipei (TW); National Taiwan University Hospital, Taipei (TW)

(72) Inventors: Yi-Jin Huang, New Taipei (TW); Chien-Hung Li, New Taipei (TW); Wei-Hao Chang, New Taipei (TW); Hung-Sheng Hsu, New Taipei (TW); Ming-Chi Kuo, New Taipei (TW); Jehn-Yu Huang, Taipei (TW)

(73) Assignees: Acer Incorporated, New Taipei (TW); National Taiwan University Hospital, Taipei (TW)

( * ) Notice: Subject to any disclaimer, the term of this patent is extended or adjusted under 35 U.S.C. 154(b) by 440 days.

(21) Appl. No.: 17/506,703

(22) Filed: Oct. 21, 2021

(65) Prior Publication Data

US 2023/0066166 A1    Mar. 2, 2023

(30) Foreign Application Priority Data

Aug. 26, 2021  (TW) .................................. 110131705

(51) Int. Cl.
*G06T 7/00*     (2017.01)
*A61B 3/00*     (2006.01)
*A61B 3/12*     (2006.01)
*A61B 3/14*     (2006.01)
*A61B 5/00*     (2006.01)

(52) U.S. Cl.
CPC .......... *G06T 7/0012* (2013.01); *A61B 3/0025* (2013.01); *A61B 3/12* (2013.01);
(Continued)

(58) Field of Classification Search
CPC ......... G06T 7/0012; G06T 2207/10024; G06T 2207/20084; G06T 2207/30041;
(Continued)

(56) References Cited

U.S. PATENT DOCUMENTS 11,610,306 B2 *  3/2023  Wang ........................ G06T 7/73
11,771,318 B2 * 10/2023  Park ....................... G16H 30/40
                                                           351/206
(Continued)

OTHER PUBLICATIONS

Nikita Moshkov et al., "Test-time augmentation for deep learning-based cell segmentation on microscopy images", Scientific Reports, Mar. 19, 2020, pp. 1-7. Available at: https://www.nature.com/articles/s41598-020-61808-3.pdf.
(Continued)

*Primary Examiner* — Dhaval V Patel
(74) *Attorney, Agent, or Firm* — JCIPRNET (57) ABSTRACT

The disclosure provides an eye state assessment method and an electronic device. The method includes: obtaining an optic disc image area from a first fundus photography and generating multiple optic cup-to-disc ratio assessment results by multiple first models based on the optic disc image area; obtaining a first assessment result of an eye based on the optic cup-to-disc ratio assessment results; performing multiple data augmentation operations on the first fundus photography to generate multiple second fundus photographies; generating multiple retinal nerve fiber layer (RNFL) defect assessment results by multiple second models based on the second fundus photographies; obtaining a second assessment result of the eye based on the RNFL defect assessment results; and obtaining an optic nerve assessment result of the eye based on the first assessment result and the second assessment result.

10 Claims, 4 Drawing Sheets

(52) U.S. Cl.
CPC .............. *A61B 3/14* (2013.01); *A61B 5/7275* (2013.01); *G06T 2207/10024* (2013.01); *G06T 2207/20084* (2013.01); *G06T 2207/30041* (2013.01)

(58) Field of Classification Search
CPC ........ G06T 2207/20081; A61B 3/0025; A61B 3/12; A61B 3/14; A61B 5/7275; G06V 10/809; G06V 10/82; G06V 40/18; G06V 40/193; G16H 30/40; G16H 50/30; G16H 50/20
See application file for complete search history.

(56) References Cited

U.S. PATENT DOCUMENTS

| | | | | |
|---|---|---|---|---|
| 11,839,430 | B2* | 12/2023 | Walsh | ................... A61B 3/117 |
| 11,887,299 | B2* | 1/2024 | Yu | ........................... G06N 3/08 |
| 2016/0100753 | A1 | 4/2016 | Liu et al. | |
| 2019/0057188 | A1* | 2/2019 | Banerjee | ............ C07K 14/1816 |
| 2020/0401841 | A1 | 12/2020 | Lee et al. | |
| 2022/0398783 | A1* | 12/2022 | Hu | ......................... G06T 3/4046 |
| 2023/0047141 | A1* | 2/2023 | Cordeiro | ................ G06V 20/69 |

OTHER PUBLICATIONS

Rutuja Shinde, "Glaucoma detection in retinal fundus images using U-Net and supervised machine learning algorithms", Intelligence-based Magazine, vol. 5 Jul. 14, 2021, pp. 100038.

Yu-Chieh Ko et al., "Deep learning assisted detection of glaucomatous optic neuropathy and potential designs for a generalizable model", PLOS ONE, May 14, 2020, pp. 1-15. Available at: https://www.ncbi.nlm.nih.gov/pmc/articles/PMC7224540/pdf/pone.0233079.pdf.

"Search Report of Europe Counterpart Application", issued on May 30, 2022, p. 1-p. 11.

* cited by examiner

EYE STATE ASSESSMENT METHOD AND ELECTRONIC DEVICE

CROSS-REFERENCE TO RELATED APPLICATION

This application claims the priority benefit of Taiwan application serial no. 110131705, filed on Aug. 26, 2021. The entirety of the above-mentioned patent application is hereby incorporated by reference herein and made a part of this specification.

BACKGROUND

1. Technical Field

The disclosure relates to a method and an electronic device for assessing the state of the human body, and more particularly to a method and an electronic device for assessing the eye state.

2. Description of Related Art

According to statistics, glaucoma is the second leading cause of blindness in Taiwan and the United States. Generally, glaucoma is diagnosed using optical coherence tomography (OCT) to calculate the thickness of retinal nerve fiber layer (RNFL), but most people do not intentionally take OCT images.

Compared with the high cost and difficulty of obtaining OCT, color fundus photography is relatively easy to obtain. Many symptoms of eye diseases can be observed in fundus photographies. The cup-to-disc ratio (CDR) and RNFL defect of optic disc to optic cup can be obtained from the fundus photography to determine the degree of glaucoma.

However, since the degree of glaucoma may vary from doctor to doctor based on fundus photographies, the design of a mechanism to assist the doctor in making the determination is an important issue for those skilled in the art.

SUMMARY

In view of the above, the disclosure provides an eye state assessment method and an electronic device which can be used to solve the above technical problems.

The disclosure provides an eye state assessment method for an electronic device, including: obtaining a first fundus photography of an eye, in which the first fundus photography includes an optic disc image area; obtaining the optic disc image area from the first fundus photography and generating multiple optic cup-to-disc ratio assessment results by multiple first models based on the optic disc image area; obtaining a first assessment result of the eye based on the optic cup-to-disc ratio assessment results; performing multiple data augmentation operations on the first fundus photography to generate multiple second fundus photographies respectively corresponding to the data augmentation operations; generating multiple retinal nerve fiber layer defect assessment results by multiple second models based on the second fundus photographies; obtaining a second assessment result of the eye based on the multiple retinal nerve fiber layer defect assessment results; and obtaining an optic nerve assessment result of the eye based on the first assessment result and the second assessment result.

The disclosure provides an electronic device, including a storage circuit and a processor. The storage circuit stores a program code. The processor is coupled to the storage circuit and accesses the program code to execute: obtaining a first fundus photography of an eye, in which the first fundus photography includes an optic disc image area; obtaining the optic disc image area from the first fundus photography and generating multiple optic cup-to-disc ratio assessment results area by multiple first models based on the optic disc image; obtaining a first assessment result of the eye based on the optic cup-to-disc ratio assessment results; performing multiple data augmentation operations on the first fundus photography to generate multiple second fundus photographies respectively corresponding to the data augmentation operations; generating multiple retinal nerve fiber layer defect assessment results by multiple second models based on the second fundus photographies; obtaining a second assessment result of the eye based on the retinal nerve fiber layer defect assessment results; and obtaining an optic nerve assessment result of the eye based on the first assessment result and the second assessment result.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Reference will now be made in detail to the exemplary embodiments of the disclosure, examples of which are illustrated in the accompanying drawings. Wherever possible, the same reference numbers are used in the drawings and the description to refer to the same or like parts.

Figure 1:
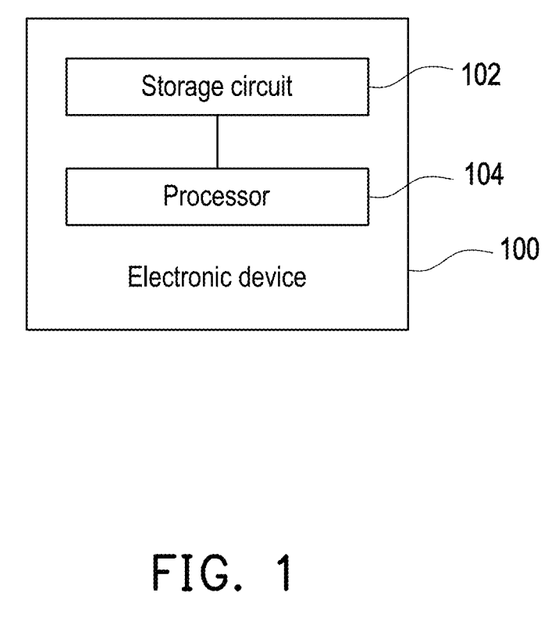
FIG. 1 is a schematic diagram of an electronic device according to an embodiment of the disclosure.

Referring to FIG. 1, which is a schematic diagram of an electronic device according to an embodiment of the disclosure. In different embodiments, an electronic device 100 may be, for example, a variety of computer devices and/or smart devices, but the disclosure may not be limited thereto.

As shown in FIG. 1, the electronic device 100 may include a storage circuit 102 and a processor 104. The storage circuit 102 may be, for example, any type of fixed or removable random access memory (RAM), read-only memory (ROM), flash memory, hard disk, or other similar devices or a combination thereof, which may be configured to record multiple codes or modules.

The processor 104 is coupled to the storage circuit 102, and may be a general-purpose processor, a special-purpose processor, a traditional processor, a digital signal processor, multiple microprocessors, one or more microprocessors combined with the digital signal processor cores, controllers, microcontrollers, application specific integrated circuits (ASIC), field programmable gate array (FPGA), any other types of integrated circuits, a state machine, or an advanced reduced instruction set computer (Advanced RISC Machine, ARM) and similar products.

In one embodiment of the disclosure, the processor 104 may access the modules and program codes recorded in the storage circuit 102 so as to implement the eye state assessment method proposed in the disclosure. The details of the method are as follows.

Figure 2:
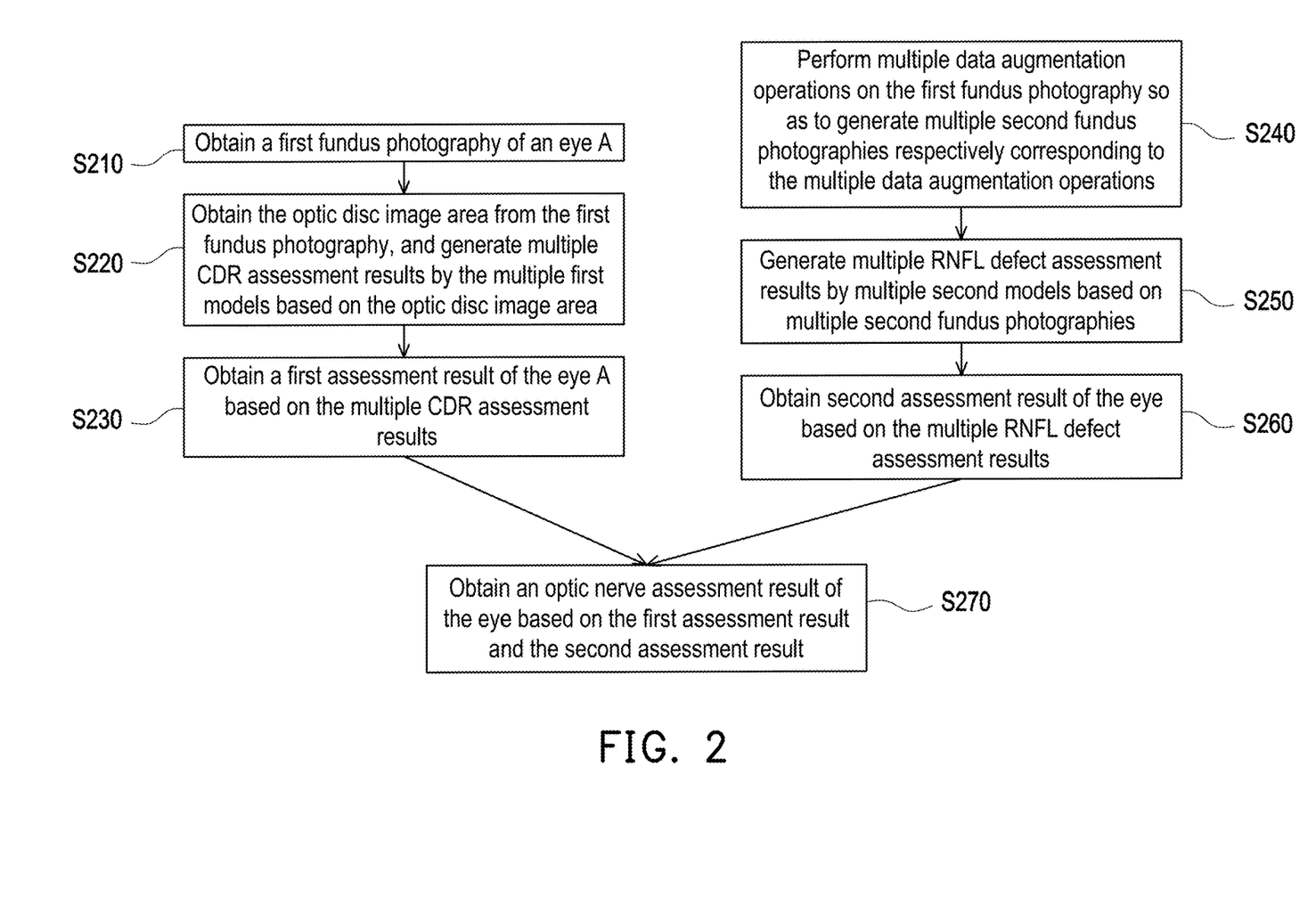
FIG. 2 is a flowchart of an eye state assessment method according to an embodiment of the disclosure.

Referring to FIG. 2, which is a flowchart of an eye state assessment method according to an embodiment of the disclosure. The method of this embodiment may be executed by the electronic device 100 of FIG. 1, and the details of each step in FIG. 2 will be explained below with the components shown in FIG. 1.

First, in step S210, the processor 104 may obtain a first fundus photography of an eye A. In one embodiment, the eye A is, for example, one of the eyes of a certain patient, and the first fundus photography is, for example, a color fundus photography obtained by medical personnel operating an instrument for taking a fundus photography of the eye A, but the disclosure may not be limited thereto.

In one embodiment, since the generally captured fundus photography may include black borders, the processor 104 may first crop the fundus photography with black borders after obtaining the fundus photography so as to generate a fundus photography without black borders as the first fundus photography, but the disclosure is not limited thereto. In order to make the concept of the disclosure easier to understand, the following will be supplemented with FIG. 3 for further explanation.

Figure 3:
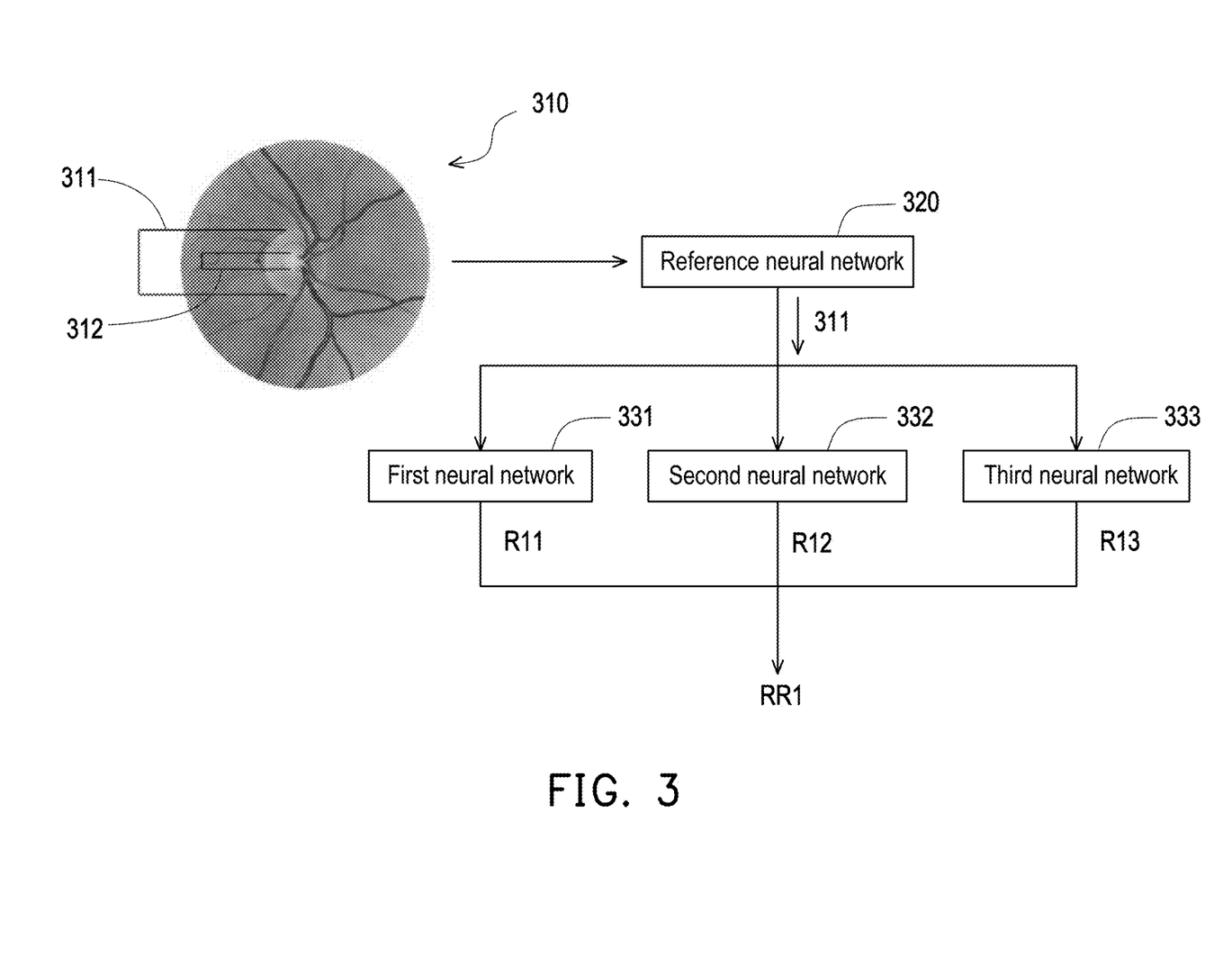
FIG. 3 is a schematic diagram of obtaining a first assessment result of the eye according to an embodiment of the disclosure.

Referring to FIG. 3, which is a schematic diagram of obtaining a first assessment result of the eye according to an embodiment of the disclosure. In FIG. 3, it is assumed that the processor 104 obtains a first fundus photography 310 shown in FIG. 3 in step S210, in which the first fundus photography 310 may include an optic disc image area 311 and an optic cup image area 312, which respectively correspond to the optic disc and the optic cup in the eye A.

After obtaining the first fundus photography 310, in step S220, the processor 104 may obtain the optic disc image area 311 from the first fundus photography 310, and generate multiple CDR assessment results by the multiple first models based on the optic disc image area 311.

In one embodiment, the processor 104 may input the first fundus photography 310 into a pre-trained reference neural network 320, in which the reference neural network 320 may identify and output the optic disc image area 311 in response to the first fundus photography 310.

In one embodiment, before the reference neural network 320 is configured to identify the optic disc image area 311 in the first fundus photography 310, the reference neural network 320 may first be trained based on training images marked with a specific region of interest (region of interest, ROI), so as to learn the characteristics of these ROIs through the training images. Therefore, in this embodiment, in order for the reference neural network 320 to have the ability to recognize the optic disc image area in any fundus photography, the reference neural network 320 may first learn based on multiple training images (i.e. fundus photographies) marked with optic disc image areas so as to learn the characteristics of the optic disc image areas in the fundus photographies, but the disclosure is not limited thereto.

After that, the processor 104 may provide the optic disc image area 311 output by the reference neural network 320 to the multiple first models so as to generate corresponding CDR assessment results. In one embodiment of the disclosure, the CDR assessment result of each first model may be that a ratio between an optic cup axial length and an optic disc axial length in the eye A (i.e. CDR) is normal or abnormal, but the disclosure may not be limited thereto.

In the scenario of FIG. 3, it is assumed that the multiple first models under consideration (the number of which is, for example, N, and N is an odd number) include a first neural network 331, a second neural network 332, and a third neural network 333 shown, but the disclosure is not limited thereto.

In one embodiment, the first neural network 331 may output a CDR assessment result R11 (for example, normal or abnormal) in response to the optic disc image area 311.

In one embodiment, in order for the first neural network 331 to have the ability to identify whether the corresponding CDR is normal in response to any optic disc image area, the first neural network 331 may first learn based on multiple optic disc image areas having normal CDR so as to learn the characteristics of the optic disc image areas with normal CDR. Moreover, the first neural network 331 may also learn based on multiple optic disc image areas having abnormal CDRs so as to learn the characteristics of the optic disc image areas with abnormal CDRs, but the disclosure is not limited thereto.

In one embodiment, the processor 104 may input the optic disc image area 311 to the second neural network 332, and the second neural network 332 may output the first CDR of the eye A in response to the optic disc image area 311.

In one embodiment, in order for the second neural network 332 to have the ability to identify the CDR in response to any optic disc image area, the second neural network 332 may first learn based on multiple optic disc image areas marked with corresponding CDRs so as to learn the characteristics of the optic disc image areas corresponding to various CDRs, but the disclosure is not limited thereto.

After obtaining the first CDR, the processor 104 may determine whether the first CDR is higher than a preset threshold (for example, 0.7). In one embodiment, in response to determining that the first CDR is higher than the preset threshold, the processor 104 may determine that a CDR assessment result R12 of the second neural network 332 is abnormal. On the other hand, in response to determining that the first CDR is not higher than the preset threshold, the processor 104 may determine that the CDR assessment result R12 of the second neural network 332 is normal, but the disclosure is not limited thereto.

In one embodiment, the processor 104 may input the optic disc image area 311 to the third neural network 333, and the third neural network 333 may output the optic cup axial length and the optic disc axial length of the eye A in response to the optic disc image area 311.

In one embodiment, in order for the third neural network 333 to have the ability to identify the optic cup axial length and the optic disc axial length in response to any optic disc image area, the third neural network 333 may first learn based on multiple optic disc image areas marked with corresponding the optic cup axial lengths and the optic disc axial lengths, so as to learn the characteristics of the optic disc image area corresponding to a variety of the optic cup axial lengths and the optic disc axial lengths, but the disclosure it not limited thereto.

After obtaining the optic cup axial length and the optic disc axial length corresponding to the optic disc image area 311, the processor 104 may obtain the second CDR of the eye A accordingly. For example, the processor 104 may divide the optic cup axial length by the optic disc axial length so as to obtain the second CDR, but the disclosure is not limited thereto.

Then, the processor 104 may determine whether the second CDR is higher than the preset threshold (for example, 0.7). In one embodiment, in response to determining that the second CDR is higher than the preset threshold, the processor 104 may determine that a CDR assessment result R13 of the third neural network 333 is abnormal. On the other hand, in response to determining that the second CDR is not higher than the preset threshold, the processor 104 may determine that the CDR assessment result R13 of the third neural network 333 is normal, but the disclosure is not limited thereto.

After obtaining the CDR assessment results R11 to R13, in step S230, the processor 104 may obtain a first assessment result RR1 of the eye A based on the multiple CDR assessment results R11 to R13.

In one embodiment, the processor 104 identifies multiple first results indicating normality in the CDR assessment results R11 to R13, and identifies multiple second results indicating abnormality in the CDR assessment results Ru to R13. Then, in response to determining that the first results are more than the second results, the processor 104 may determine that the first assessment result RR1 indicates normality (that is, the CDR of the eye A is normal). On the other hand, in response to determining that the first results are less than the second results, the processor 104 may determine that the first assessment result RR1 indicates abnormality (that is, the CDR of the eye A is abnormal).

In short, the processor 104 may make a majority decision based on the CDR assessment results R11 to R13. If there are more first results indicating normality in the CDR assessment results R11 to R13, the processor 104 may determine that the first assessment result RR1 indicates normality; if there are more second results indicating abnormality in the CDR assessment results R11 to R13, the processor 104 may determine that the first assessment result RR1 indicates abnormality, but the disclosure may not be limited thereto.

Further, in step S240, the processor 104 may perform multiple data augmentation operations on the first fundus photography 310 so as to generate multiple second fundus photographies respectively corresponding to the multiple data augmentation operations. In order to make the concept of the disclosure easier to understand, the following will be supplemented with FIG. 3 for further explanation.

Figure 4:
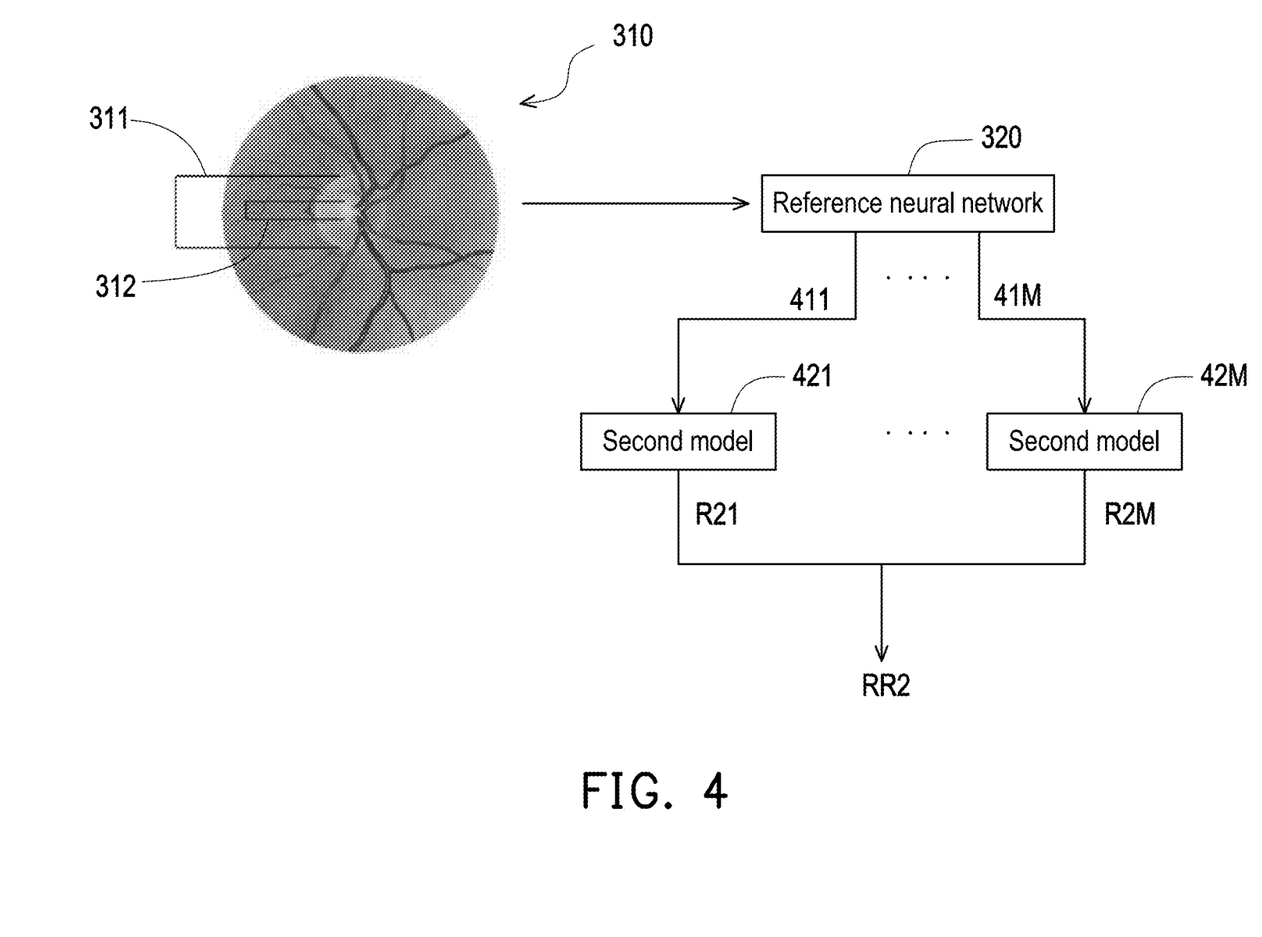
FIG. 4 is a schematic diagram of obtaining a second assessment result of the eye according to FIG. 3.

Referring to FIG. 4, which is a schematic diagram of obtaining a second assessment result of the eye according to FIG. 3. In FIG. 4, the processor 104 may perform M data augmentation operations (M is a positive integer) on the first fundus photography 310 so as to generate M second fundus photographies 411 to 41M. The M data augmentation operations may include rotating, shifting, flipping, zooming, and stretching the first fundus photography 310, but the disclosure is not limited thereto.

After that, in step 250, the processor 104 may input the second fundus photographies 411 to 41M to second models 421 to 42M, respectively, so as to output corresponding confidence values of prediction by the second models 421 to 42M as RNFL defect assessment results R21 to R2M. In one embodiment, the confidence value of prediction corresponding to each of the second models 421 to 42M (i.e. the RNFL defect assessment results R21 to R2M) may indicate the degree of abnormality of the RNFL of the eye A.

In one embodiment, in order for each of the second models 421 to 42M to have the ability to identify the degree of abnormality of the corresponding RNFL in response to the fundus photography in which data has been augmented, each of the second models 421 to 42M may first learn based on multiple (data-augmented) fundus photographies marked with the corresponding abnormalities of RNFLs so as to learn the characteristics of the fundus photography corresponding to the abnormality of a variety of RNFLs, but the disclosure is not limited thereto.

After obtaining the confidence value of prediction of each of the second models 421 to 42M (that is, the RNFL defect assessment results R21 to R2M), in step S260, the processor 104 may obtain a second assessment result RR2 of the eye A based on the multiple RNFL defect assessment results R21 to R2M.

In one embodiment, the processor 104 may obtain a squared difference between the confidence value of prediction corresponding to each of the second models 421 to 42M and a reference base value (for example, 0.5), and identify a candidate model in the second models 421 to 42M accordingly. In one embodiment, the squared difference corresponding to the candidate model may be the largest among the second models 421 to 42M.

After that, the processor 104 may determine whether the confidence value of prediction corresponding to the candidate model is higher than the reference base value. If so, the processor 104 may determine that the second assessment result RR2 of the eye A indicates abnormality; if not, the processor 104 may determine that the second assessment result RR2 of the eye A indicates normality.

After obtaining the first assessment result RR1 (which may indicate normal or abnormal) and the second assessment result RR2 (which may indicate normal or abnormal) of the eye A, in step S270, the processor 104 may obtain an optic nerve assessment result of the eye A based on the first assessment result RR1 and the second assessment result RR1.

In one embodiment, in response to determining that the first assessment result RR1 indicates normality and the second assessment result RR2 indicates normality, it is determined that the optic nerve assessment result of eye A belongs to a first risk level. In response to determining that the first assessment result RR1 indicates abnormality and the second assessment result RR2 indicates normality, it is determined that the optic nerve assessment result of eye A belongs to a second risk level, in which the second risk degree is greater than the first risk degree. In response to determining that the first assessment result RR1 indicates normality and the second assessment result RR2 indicates abnormality, it is determined that the optic nerve assessment result of eye A belongs to a third risk degree, in which the third risk degree is greater than the second risk degree. In response to determining that the first assessment result RR1 indicates abnormality and the second assessment result RR2 indicates abnormality, it is determined that the optic nerve assessment result of eye A belongs to a fourth risk level, in which the fourth risk degree is greater than the third risk degree.

In one embodiment, the first, second, third, and fourth risk levels may be understood as the probability of the eye A suffering from glaucoma. For example, when the optic nerve assessment result of the eye A belongs to the first risk level, it means that the probability of the eye A suffering from glaucoma is low. On the other hand, when the optic nerve assessment result of eye A belongs to the fourth risk level, it means that the probability of the eye A suffering from glaucoma is higher, but the disclosure is not limited thereto. In this way, the disclosure may present the obtained optic nerve assessment result to the doctor or other relevant personnel as auxiliary information for diagnosing the eye A, but the disclosure is not limited thereto.

In one embodiment, the first, second, third, and fourth risk levels may be roughly understood as normal, low-risk, medium-risk, and high-risk, which may be organized as shown in Table 1 below, but the disclosure is not limited thereto.

| First assessment result RR1 | Second assessment result RR2 | Optic nerve assessment results |
|---|---|---|
| normal | normal | normal |
| abnormal | normal | low risk |
| normal | abnormal | medium risk |
| abnormal | abnormal | high risk |

In summary, according to the disclosure, after obtaining the optic disc image area, multiple first models having different recognition mechanisms may individually generate corresponding CDR assessment results based on the optic disc image area, and then a majority decision is made to determine whether the first assessment result indicates normality or abnormality. Further, according to disclosure, multiple different data augmentations may be performed on the first fundus photography so as to obtain multiple second fundus photographies, and then a corresponding RNFL defect result based on one of the second fundus photographies may be generated by each second model, and a second assessment result indicating that the RNFL of the eye is normal or abnormal is obtained accordingly. After that, according to the disclosure, comprehensive consideration of the first and second assessment results can be taken so as to obtain the optic nerve assessment result of the eye. In this way, the disclosure can provide a reference for a doctor when assessing the patient's eye state, thereby helping the doctor to offer an appropriate assessment result to the patient's eye. For example, the doctor can make an appropriate assessment of whether or not the patient has glaucoma based on the optic nerve assessment result provided by the embodiment of the disclosure, thereby improving the quality of diagnosis.

It will be apparent to those skilled in the art that various modifications and variations may be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An eye state assessment method for an electronic device, comprising:
   obtaining a first fundus photography of an eye, wherein the first fundus photography comprises an optic disc image area;
   obtaining the optic disc image area from the first fundus photography and generating a plurality of optic cup-to-disc ratio assessment results by a plurality of first models based on the optic disc image area;
   obtaining a first assessment result of the eye based on the optic cup-to-disc ratio assessment results;
   performing a plurality of data augmentation operations on the first fundus photography to generate a plurality of second fundus photographies respectively corresponding to the data augmentation operations;
   generating a plurality of retinal nerve fiber layer defect assessment results by a plurality of second models based on the second fundus photographies, comprising:
      inputting one of the second fundus photographies into one of the second models, wherein the one of the second models outputs a confidence value of prediction as one of the retinal nerve fiber layer defect assessment results in response to the one of the second fundus photographies, wherein the confidence value of prediction indicates a degree of abnormality of the eye;
   obtaining a second assessment result of the eye based on the retinal nerve fiber layer defect assessment results, comprising:
      obtaining a square difference between the confidence value of prediction corresponding to each of the second models and a reference base value, and identifying a candidate model in the second models accordingly, wherein the square difference corresponding to the candidate model is the largest among the second modes;
      determining that the second assessment result of the eye indicates abnormality in response to determining that the confidence value of prediction corresponding to the candidate model is higher than the reference base value; and
      determining that the second assessment result of the eye indicates normality in response to determining that the confidence value of prediction corresponding to the candidate model is not higher than the reference base value; and
   obtaining an optic nerve assessment result of the eye based on the first assessment result and the second assessment result.

2. The method according to claim 1, wherein the first fundus photography comprises a color fundus photography of the eye, and the color fundus photography does not have black borders.

3. The method according to claim 1, wherein a step of obtaining the optic disc image area from the first fundus photography comprises:
   inputting the first fundus photography to a reference neural network, wherein the reference neural network recognizes the optic disc image area in the first fundus photography in response to the first fundus photography, and outputs the optic disc image area.

4. The method according to claim 1, wherein the first models comprise N neural networks, and each of the optic cup-to-disc ratio assessment results indicates whether an optic cup-to-disc ratio of the eye is normal or abnormal, wherein N is an odd number.

5. The method according to claim 4, wherein a step of obtaining the first assessment result of the eye based on the optic cup-to-disc ratio assessment results comprises:
   identifying a plurality of first results indicating normality from the optic cup-to-disc ratio assessment results, and identifying a plurality of second results indicating abnormality from the optic cup-to-disc ratio assessment results;
   determining that the first assessment result indicates normality in response to determining that the first results are more than the second results; and
   determining that the first assessment result indicates abnormality in response to determining that the first results are less than the second results.

6. The method according to claim 1, wherein the first models comprise a first neural network, and the method comprises:
   inputting the optic disc image area to the first neural network, wherein the first neural network outputs one of the optic cup-to-disc ratio assessment results in response to the optic disc image area.

7. The method according to claim 1, wherein the first models comprise a second neural network, and the method comprises:
inputting the optic disc image area into the second neural network, wherein the second neural network outputs a first optic cup-to-disc ratio of the eye in response to the optic disc image area;
determining that one of the optic cup-to-disc ratio assessment results corresponding to the second neural network indicates abnormality in response to determining that the first optic cup-to-disc ratio is higher than a preset threshold; and
determining that one of the optic cup-to-disc ratio assessment results corresponding to the second neural network indicates normality in response to determining that the first optic cup-to-disc ratio is not higher than the preset threshold.

8. The method according to claim 1, wherein the optic disc image area comprises an optic cup image area, the first models comprise a third neural network, and the method comprises:
inputting the optic disc image area into the third neural network, wherein the third neural network outputs an optic cup axial length of the eye in response to the optic cup image area, and outputs an optic disc axial length of the eye in response to the optic disc image area;
obtaining a second optic cup-to-disc ratio of the eye based on the optic cup axial length and the optic disc axial length;
determining that one of the optic cup-to-disc ratio assessment results corresponding to the third neural network indicates abnormality in response to determining that the second optic cup-to-disc ratio is higher than a preset threshold; and
determining that one of the optic cup-to-disc ratio assessment results corresponding to the third neural network indicates normality in response to determining that the second optic cup-to-disc ratio is not higher than the preset threshold value.

9. The method described in claim 1, wherein the first assessment result indicates normality or abnormality, the second assessment result indicates normality or abnormality, and a step of obtaining an optic nerve assessment result of the eye based on the first assessment result and the second assessment result comprises:
determining that the optic nerve assessment result of the eye belongs to a first risk level in response to determining that the first assessment result indicates normality and the second assessment result indicates normality;
determining that the optic nerve assessment result of the eye belongs to a second risk degree in response to determining that the first assessment result indicates abnormality and the second assessment result indicates normality, wherein the second risk degree is greater than the first risk degree;
determining that the optic nerve assessment result of the eye belongs to a third risk degree in response to determining that the first assessment result indicates normality and the second assessment result indicates abnormality, wherein the third risk degree is greater than the second risk degree; and
determining that the optic nerve assessment result of the eye belongs to a fourth risk degree in response to determining that the first assessment result indicates abnormality and the second assessment result indicates abnormality, wherein the fourth risk degree is greater than the third risk degree.

10. An electronic device, comprising:
a storage circuit, storing a program code;
a processor, coupled to the storage circuit and accessing the program code to execute:
obtaining a first fundus photography of an eye, wherein the first fundus photography comprises an optic disc image area;
obtaining the optic disc image area from the first fundus photography and generating a plurality of optic cup-to-disc ratio assessment results by a plurality of first models based on the optic disc image area;
obtaining a first assessment result of the eye based on the optic cup-to-disc ratio assessment results;
performing a plurality of data augmentation operations on the first fundus photography to generate a plurality of second fundus photographies respectively corresponding to the data augmentation operations;
generating a plurality of retinal nerve fiber layer defect assessment results by a plurality of second models based on the second fundus photographies, comprising:
inputting one of the second fundus photographies into one of the second models, wherein the one of the second models outputs a confidence value of prediction as one of the retinal nerve fiber layer defect assessment results in response to the one of the second fundus photographies, wherein the confidence value of prediction indicates a degree of abnormality of the eye;
obtaining a second assessment result of the eye based on the retinal nerve fiber layer defect assessment results, comprising:
obtaining a square difference between the confidence value of prediction corresponding to each of the second models and a reference base value, and identifying a candidate model in the second models accordingly, wherein the square difference corresponding to the candidate model is the largest among the second modes;
determining that the second assessment result of the eye indicates abnormality in response to determining that the confidence value of prediction corresponding to the candidate model is higher than the reference base value; and
determining that the second assessment result of the eye indicates normality in response to determining that the confidence value of prediction corresponding to the candidate model is not higher than the reference base value; and
obtaining an optic nerve assessment result of the eye based on the first assessment result and the second assessment result.

* * * * *